United States Patent [19]

Hölscher

[11] Patent Number: 4,647,363
[45] Date of Patent: Mar. 3, 1987

[54] ELECTROCHEMICAL MEASURING CELL

[75] Inventor: Uvo Hölscher, Stockelsdorf, Fed. Rep. of Germany

[73] Assignee: Drägerwerk Aktiengesellschaft, Lübeck, Fed. Rep. of Germany

[21] Appl. No.: 771,994

[22] Filed: Sep. 3, 1985

[30] Foreign Application Priority Data

Sep. 7, 1984 [DE] Fed. Rep. of Germany ....... 3432949

[51] Int. Cl.$^4$ ........................................... G01N 27/46
[52] U.S. Cl. .................................. 204/415; 204/1 T; 204/432
[58] Field of Search ..................... 204/1 P, 415, 432

[56] References Cited

U.S. PATENT DOCUMENTS

| | | | |
|---|---|---|---|
| 3,468,781 | 9/1969 | Lucero | 204/415 |
| 3,510,420 | 5/1970 | Mills | 204/415 |
| 3,574,078 | 4/1971 | Hynes et al. | 204/415 |
| 3,590,810 | 7/1971 | Kopecky | 204/415 |
| 3,708,412 | 1/1973 | Lofgren | 204/415 |
| 4,036,724 | 7/1977 | Binder et al. | 204/432 |
| 4,201,634 | 5/1980 | Stetter | 204/432 |
| 4,404,066 | 9/1983 | Johnson | 204/415 |
| 4,517,982 | 5/1985 | Shiga et al. | 128/635 |
| 4,538,617 | 9/1985 | Jensen | 128/635 |

FOREIGN PATENT DOCUMENTS

| | | | |
|---|---|---|---|
| 2930663 | 2/1981 | Fed. Rep. of Germany | 128/635 |
| 54344 | 5/1981 | Japan | 204/415 |
| 56748 | 4/1982 | Japan | 204/415 |

OTHER PUBLICATIONS

Jakobs et al., "Oxygen Reduction at Polypyrrole Electrodes-II. Experimental Results", *Electrochim Acta*, No. 11, Nov. 1985, pp. 1433–1439.

*Primary Examiner*—T. Tung
*Attorney, Agent, or Firm*—Walter Ottesen

[57] ABSTRACT

An electrochemical measuring cell is disclosed wherein the diffusion membrane which separates the electrolyte from the ambient is made of an intrinsically-conductive and electrochemically active plastic. This way the diffusion membrane itself defines the measuring electrode of the measuring cell. This is a substantial advantage over known electrochemical measuring cells wherein the measuring electrode is defined by an electrically conductive layer applied to the surface of the diffusion membrane facing toward the electrolyte. By making the diffusion membrane from an electrochemically active plastic, a removal of the electrically-conductive layer from the diffusion membrane is prevented.

4 Claims, 1 Drawing Figure

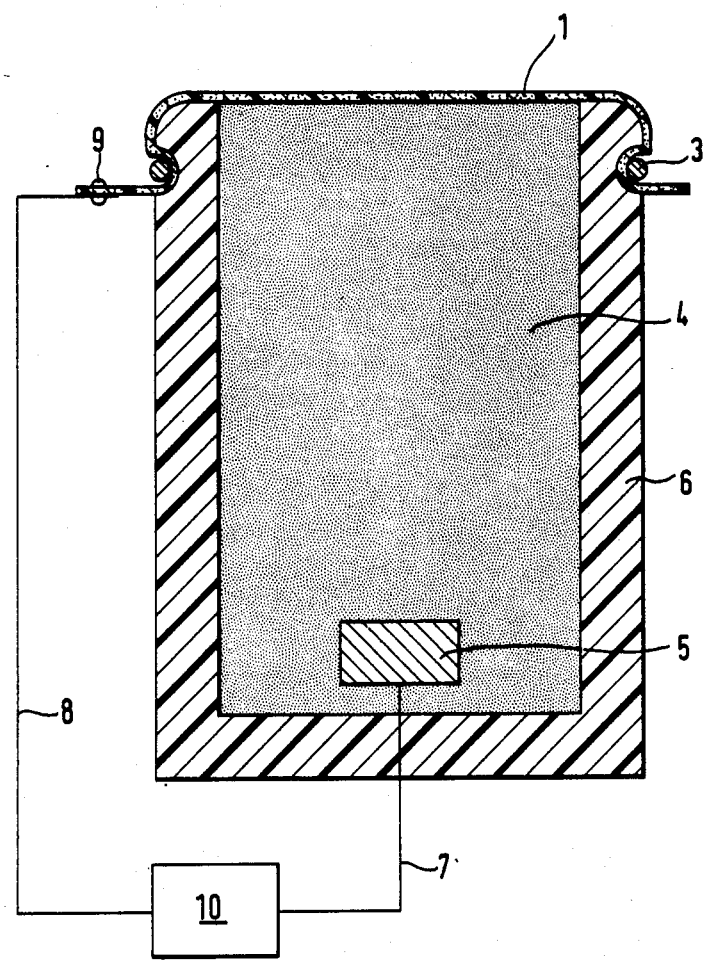

ELECTROCHEMICAL MEASURING CELL

FIELD OF THE INVENTION

The invention relates to an electrochemical measuring cell which includes a measuring electrode and a counter electrode in an electrolyte. The electrolyte is separated from the ambient by a diffusion membrane.

BACKGROUND OF THE INVENTION

Measuring cells of this type utilize so-called Clark-electrodes for measuring the concentration or partial pressure of gases.

In known Clark-electrode arrangements, the measuring electrode is made of a thin platinum wire which is brought up to a predetermined spacing in the electrolyte with respect to the inner surface of the diffusion membrane. In this connection, maintaining this spacing between the platinum wire point and the membrane surface is important. Any change of the spacing causes a change in the measured value and can be brought about, for example, by a mechanical loading of the diffusion membrane.

United Kingdom Pat. No. 1,200,595 discloses that this disadvantage can be improved upon by configuring the measuring electrode as an electrically conducting layer applied to the surface of the diffusion membrane facing toward the electrolyte. Since an electrolyte, the electrode material corresponding to the electrolyte and the required diffusion membrane are all determined by the measuring task, the selection of an electrode material as well as the membrane material can no longer be made alone with respect to the view point of a good adherence of the electrically-conductive metal film on the diffusion membrane. Accordingly, the possibility of combinations of electrolyte, electrode material and diffusion membrane which ensure a reliable adherence of the electrically-conducting film on the diffusion membrane is limited. Electrically-conductive layers which adhere poorly must be supported with an additionally applied porous protective membrane.

SUMMARY OF THE INVENTION

It is an object of the invention to provide an electrochemical measuring cell of the type described above which is improved so that the measuring electrode forms a tight bond with the diffusion membrane thereby making an additional protective membrane no longer necessary and so that the selection of suitable electrolytes, measuring electrodes and diffusion membranes is not limited by inadequate adherence conditions of the measuring electrode.

The foregoing object is realized in the measuring cell according to the invention by providing the diffusion membrane in the form of a measuring electrode. The diffusion membrane is made of an electrochemically active plastic which is intrinsically electrically conductive.

The diffusion membrane of the electrochemical measuring cell of the invention is itself either made of electrochemically active material or is activated, for example, by means of an ion-injection of a catalytic material.

Preferably, the diffusion membrane comprises a mixture of polypyrrole and a catalyzer with the latter being added to the polypyrrole in the form of admixtures of precious metals or carbon particles. A further advantageous possibility of activation is to mix a predetermined quantity of iron phthalocyanine with the polypyrrole.

Such electrochemically active, intrinsically conductive plastic membranes can be expanded with respect to their application in that they can be utilized to sense electrical potentials as with an ECG-electrode.

BRIEF DESCRIPTION OF THE DRAWING

The drawing consists of one figure showing an elevation view, partially in section, of an embodiment of the electrochemical measuring cell of the invention.

DESCRIPTION OF THE PREFERRED EMBODIMENTS OF THE INVENTION

The electrochemical measuring cell shown in the drawing includes a housing 6 which accommodates the electrolyte 4 and a counter electrode 5. One end of the housing 6 is closed off with respect to the ambient by means of a diffusion membrane 1. The diffusion membrane 1 is attached to the housing 6 by means of a clamping ring 3. Since the electrochemically active diffusion membrane 1 is configured as a measuring electrode to be electrically conductive, the electrode signal can be conducted to a measuring apparatus 10 via a contact 9 and a lead 8. The counter electrode 5 is connected to the measuring apparatus 10 via a lead 7.

It is understood that the foregoing description is that of the preferred embodiments of the invention and that various changes and modifications may be made thereto without departing from the spirit and scope of the invention as defined in the appended claims.

What is claimed is:

1. An electrochemical measuring cell comprising:
   an electrolyte;
   a counter electrode disposed in said electrolyte;
   holding means for holding the electrolyte; and,
   a diffusion membrane for separating said electrolyte from the ambient; and,
   said diffusion membrane being made of an intrinsically electrically conductive and electrochemically active plastic so as to cause said diffusion membrane itself to be a measuring electrode.

2. The electrochemical measuring cell of claim 1, said electrochemically active plastic comprising a mixture of polypyrrole and a catalyst.

3. The electrochemical measuring cell of claim 2, said catalyst being iron phthalocyanine.

4. An electrochemical measuring cell comprising:
   an electrolyte;
   a counter electrode disposed in said electrolyte;
   a housing for accommodating said electrolyte and said counter electrode therein;
   a diffusion membrane attached to said housing for closing off the latter so as to separate said electrolyte from the ambient;
   said diffusion membrane being made of an eletrochemically active plastic which is intrisically electrically conductive so as to cause said membrane to constitute a measuring electrode; and,
   circuit means connected to said measuring electrode for conducting an electrode signal away from the latter.

* * * * *